United States Patent [19]

Van Buren et al.

[11] Patent Number: 5,354,935

[45] Date of Patent: Oct. 11, 1994

[54] CATALYSTIC METHOD FOR THE DEHYDROGENATION OF HYDROCARBONS

[75] Inventors: Frederik R. Van Buren; Dick E. Stobbe, both of Terneuzen; John W. Geus, Bilthoven; Adrianus J. Van Dillen, Culemborg, all of Netherlands

[73] Assignee: The Dow Chemical Company, Midland, Mich.

[21] Appl. No.: 105,554

[22] Filed: Aug. 12, 1993

Related U.S. Application Data

[62] Division of Ser. No. 849,037, Apr. 21, 1992, Pat. No. 5,238,348.

[51] Int. Cl.$^5$ ............................................. C07C 5/02
[52] U.S. Cl. ............................... 585/444; 585/440; 585/445; 585/630; 585/631
[58] Field of Search ............... 585/440, 444, 445, 629, 585/630, 631, 661, 662, 663

[56] References Cited

U.S. PATENT DOCUMENTS

| | | | |
|---|---|---|---|
| 2,395,875 | 3/1946 | Kearby et al. | 585/444 |
| 2,436,616 | 2/1948 | Sumerford | 585/445 |
| 2,461,147 | 2/1949 | Davies et al. | 585/631 |
| 4,107,087 | 8/1978 | Pessimisis | 502/215 |
| 4,460,706 | 7/1984 | Imanari et al. | 503/304 |
| 5,146,031 | 9/1992 | Khajai et al. | 585/624 |

FOREIGN PATENT DOCUMENTS

| | | |
|---|---|---|
| 0181999 | 5/1986 | European Pat. Off. |
| 0194829 | 9/1986 | European Pat. Off. |
| 0224947 | 6/1987 | European Pat. Off. |
| 1554095 | 1/1969 | France |
| 2200047 | 4/1974 | France |
| 2249863 | 5/1975 | France |
| 9006907 | 6/1990 | World Int. Prop. O. |

OTHER PUBLICATIONS

K. K. Kearby, "Catalytic Dehydrogenation of Butenes", Industrial and Engineering Chemistry, vol. 42, No. 2, (1950), pp. 295-300.

Primary Examiner—Asok Pal
Assistant Examiner—P. Achutamurthy

[57] ABSTRACT

A catalyst comprising a preshaped porous support material having applied thereto in finely divided form an active compound chosen from at least one compound of vanadium, chromium, manganese, iron, cobalt, nickel, copper and zinc, and optionally a promoter chosen from at least an alkali or alkaline earth metal compound, method for the preparation thereof and use thereof in the dehydrogenation of hydrocarbons.

20 Claims, 9 Drawing Sheets

CATALYSTIC METHOD FOR THE DEHYDROGENATION OF HYDROCARBONS

CROSS-REFERENCE TO RELATED APPLICATION

This is a division of application Ser. No. 07/849,037, filed Apr. 21, 1992, now U.S. Pat. No. 5,238,348.

The present invention relates to a supported catalyst, to a method for the preparation thereof and to the use thereof in the dehydrogenation of hydrocarbons.

The dehydrogenation of compounds like hydrocarbons is a widely used and large scale type of process. Examples of such dehydrogenation processes include: the dehydrogenation of alkanes to alkenes, such as propane to propene and butane to butene, the dehydrogenation of alkenes to corresponding alkadienes, such as from butene to 1, 3-butadiene, the dehydrogenation of alkyl-aromatic hydrocarbons to alkenyl-aromatic hydrocarbons, such as from ethylbenzene to styrene. Hereinafter the invention will be further explained by reference to the dehydrogenation of ethylbenzene to styrene, unless mentioned otherwise.

The catalysts used for such a large scale process are based on iron oxide as active component. U.S. Pat. No. 2,395,875 discloses a dehydrogenation catalyst consisting of magnesium oxide as base material (support material), iron oxide as active component and a small quantity of an alkali or alkaline earth metal oxide as promoter. Optionally the catalyst further contains a small quantity of a transition metal oxide as stabilizer. The alkali- or alkaline earth metal oxide promoter also serves to reduce to the minimum, together with steam supplied to the process, the precipitation on the catalyst of the carbon-containing byproducts. In U.S. Pat. No. 2,395,875 the catalyst is prepared by mixing powdered magnesium oxide with a solution of iron(III) nitrate, after which complete precipitation is achieved by addition of lye. Then the mixture is treated with solutions of the stabilizer and of the promoter. The resulting mixture is dried, heated and subsequently formed into pills or pellets of the desired dimensions and shape. However, these dehydrogenation catalysts deactivate quickly, which also becomes evident from the article "Catalytic Dehydrogenation of Butenes", K. K. Kearby, Industrial and Engineering Chemistry Vol. 42, No. 2 (1950), pages 295-300.

At present, the most widely used type of catalyst for the dehydrogenation of hydrocarbons and especially of ethylbenzene to styrene is an unsupported catalyst based on iron(III) oxide, chromium(III) oxide and potassium oxide, as described in U.S. Pat. No. 2,461,147. The use of such unsupported catalysts in large fixed-bed reactors, such as in the dehydrogenation of ethylbenzene to styrene where in the reactors catalyst beds of for example 10 to 200 tons are used has, however, some disadvantages. Under reaction conditions the major catalyst component, α-iron(III) oxide (hematite, $Fe_2O_3$) usually undergoes a reduction to $Fe_3O_4$ (magnetite). As a consequence, the hexagonal lattice structure of hematite is converted to the cubic lattice structure of magnetite. The mechanical strength of the catalyst bodies is reduced considerably by this conversion or recrystallization, as iron oxide is the main catalyst component. Because of the high mechanical forces in the catalyst bed, on the long run this recrystallization contributes to the disintegration or pulverization of the catalyst bodies. This in its turn results in an increase of the pressure drop over the catalyst bed, which adversely affects the selectivity and yield of the catalytic dehydrogenation process. When the pressure drop becomes too high the catalyst bed should be replaced, which is a time consuming and costly operation. Further, during the reduction of the iron oxide also metallic iron may be formed, which is known to stimulate the formation of carbon.

A further disadvantage associated with this type of unsupported catalyst is the migration of the promoter, usually a potassium compound such as potassium (hydr)oxide or carbonate. Under reaction conditions the potassium compound is slightly volatile. As the catalytic reaction is endothermal, thereby requiring heat to be supplied to the reaction mixture, and as the thermal conductivity of the catalyst particles is limited, a temperature gradient may develop in the catalyst bed. This temperature gradient will exist in the catalyst particles themselves and, dependent on the type of reactor, over the length of the catalyst bed. As a consequence thereof, a downstream part of the catalyst bed may have a lower temperature than an upstream part. Also the interior of a catalyst particle may have a lower temperature than the exterior part thereof. Due to the fact that the potassium compound is volatile under reaction conditions it will migrate to the colder (interior) part of the catalyst particles and to the colder parts of the catalyst bed. As a result of the migration of the promoter, the deposition of carbon containing products can take place to a higher degree at the exterior of the catalyst particles and in the hotter parts of the catalyst bed. Consequently the pore openings of the catalyst particles may become plugged, which may lead to deactivation of the catalyst. This deactivation process may partially be counteracted by gradually increasing the reaction temperature during the life time of the catalyst. In that way the conversion remains high, however, the selectivity is decreased. Further, the migration of the promoter leads to a local increase of porosity of the catalyst particles and, consequently, to a reduction of the mechanical strength in the potassium depleted zones.

FR-A 2249863 discloses a catalyst for the dehydrogenation of ethylbenzene to styrene, wherein the metal oxide active component is deposited on an inert support in a layer having a thickness of 0.01-2 mm. In such a catalyst, however, recrystallization under reaction conditions of the active component, which is present in a relatively thick outer layer, will lead to attrition problems.

The present invention now has the object to provide a catalyst which does not, or to a lesser degree, entail the above-mentioned disadvantages. Thus the catalyst according to the invention comprises a preshaped porous support material to which has been applied in a finely divided form at least a catalytically active component chosen from the group of compounds of the transition metals vanadium, chromium, manganese, iron, cobalt, nickel, copper and zinc, and optionally at least an alkali metal and/or alkaline earth metal compound as promoter.

Having been applied onto a preshaped porous support material in finely divided form, a recrystallization of the small particles of the catalytically active component does not lead to a noticeable decrease of the mechanical strength. In case also a promoter has been applied, it has surprisingly been found that the migration of the promoter, if at all occuring, does not result in a decreased mechanical strength of the catalyst.

BRIEF DESCRIPTION OF THE DRAWINGS

The results of 1-butene dehydrogenation experiments using the present invention are illustrated in FIG. 1-7, in which.

As used herein, with preshaped porous support material is meant a non-powderous body of support material which, after application of the catalytically active component and optionally a promoter, requires no further shaping operation in view of the catalytic process in which it is to be used. Such a preshaped porous support material can be produced by subjecting a corresponding powderous support material to a shaping operation and/or a thermal treatment, causing sintering of the powder particles. The body so formed can be reduced to smaller preshaped bodies, if desired, by means of well known techniques. Preshaped porous supports as herein defined are well known in the art and commercially available.

As preshaped porous support material each thermo-stable, mechanically strong support material may be used which does not react with the catalytically active component and the optionally applied promoter such that the final catalyst material is not or insufficiently active. The terms thermo-stable and mechanically strong refer to the conditions of use of the catalyst. This means that in case of the dehydrogenation of e.g. ethylbenzene to styrene, the preshaped support should be resistant to temperatures of 400°-800° C. and to the forces prevailing in a commercial catalyst bed of e.g. more than 10 tons. Examples of support materials which are suitable for the catalyst according to the invention include: alkaline earth metal oxides such as magnesium oxide, calcium oxide, strontium oxide and barium oxide, oxides of rare earth metals, zirconium oxide, titanium dioxide and titanares. One can also use suitable spinels as support material, such as magnesium aluminate ($MgAl_2O_4$). Preferably a non-acidic and more preferably a basic support material is used. Most preferably magnesium oxide is used as support material. It will be understood, that the above-mentioned support materials can also be applied as an adhering layer onto other thermo-stable, mechanically strong preshaped support materials, on which layer then the catalytically active component and optionally the promoter are applied. A particularly suitable method to apply such a support material layer onto a preshaped carrier is described in EP-A- 224947 of The Dow Chemical Company. Especially, preshaped support bodies of α-aluminum oxide are suited herefor.

In the dehydrogenation processes and in particular in the dehydrogenation of ethylbenzene to styrene, catalyst particles having relatively wide pores and a relatively low specific surface area are generally required in connection with the fast transport of the reactants and products. Relatively small pores are disadvantageous for the selectivity to and the yield of the desired end product.

Therefore, the specific surface area (BET) of the preshaped support material is preferably not more than 50 $m^2$ per gram, more preferably from 0.1 to 25 $m^2$ per gram and most preferably the specific surface area is from 1 to 10 $m^2$ per gram. In view of the end use the value of the specific surface area of the preshaped porous support may be adjusted as desired by means of methods well-known in the art referred to above, such as a heat treatment.

On the other hand, the catalyst particles should not be too small as the pressure drop over the catalyst bed then becomes too large. Therefore, the preshaped support particles according to the present invention generally have an average diameter of at least 0.5 mm, preferably from 1 to 20 mm and more preferably from 1 to 10 mm. It will be clear that one can also use larger support bodies and thus catalyst bodies without adversely affecting the selectivity, by employing specially shaped support bodies of the desired strength, such as for example hollow cylinders or special cylindrically shaped tablets which are commercially available.

As catalytically active component in the catalyst according to the invention, a compound of vanadium, chromium, manganese, iron, cobalt, nickel, copper or zinc is generally used, and preferably one or more oxides of one or more of the above-mentioned metals. According to the invention it is preferred that at least an oxide of iron has been applied to the preshaped support material. For applying the catalytically active component as well as optionally the promoter on the support material, compounds or complexes of the (transition) metal components of these catalyst components which are soluble in water or in liquids having not too high a boiling point can generally be used.

In general the catalytically active component is present in a quantity from 0.1 to 60 wt.% based on the total catalyst weight and calculated as zero-valent transition metal. Preferably an oxide of iron is present in a quantity from 0.1 to 20 wt.% and most preferably in a quantity from 0.5 to 8 wt.% based on the total catalyst weight, calculated as iron(O).

Within the group of alkali and alkaline earth metal compounds which optionally have been applied as promoter, the alkali metal compounds are preferred. Within this group of compounds the (hydr)oxides and carbonates and especially the (hydr)oxide and carbonate of potassium are preferred as promoter. One can apply the potassium compound by means of solutions of potassium hydroxide or of an other suitable potassium salt, such as -carbonate and -nitrate. Potassium in a soluble complex may also be used for this purpose.

The promoter, if desired, is preferably present in a quantity from 0.1 to 20 wt.%, based on the total catalyst weight, calculated as zero-valent metal. More preferably, a potassium promoter is present in a quantity of 0.1 to 10 wt.% and most preferably in a quantity of 1 to 5 wt.%, based on the total catalyst weight, calculated as potassium(O).

According to a further aspect the present invention relates to a method for the preparation of the above-mentioned catalyst, wherein the preshaped porous support material is at least once impregnated with a solution containing the catalytically active component or precursor thereof, followed by removing the solvent by means of vaporization and/or heating, and optionally, prior to, simultaneously with and/or following the above-mentioned impregnation step the preshaped porous support material is at least once impregnated with a solution containing the promoter or a precursor thereof, thereafter the solvent is removed by means of vaporization and/or heating, optionally followed by conversion of the respective precursor to the catalytically active component or promoter, respectively.

In the terminology used herein, with precursor is meant the metal or a compound or complex of the metal which metal is present in the final catalyst component. During the catalyst preparation or in a separate step or under reaction conditions this precursor is converted to the catalytically active component or promoter, for example by means of a thermal treatment or another reaction.

For the purpose of applying the active component or components and optionally the promoter to the preshaped porous support material, one can employ any method known per se which is suitable to distribute such components in finely divided form over the surface, including the pore surfaces of the preshaped porous support body. However, a method particularly suitable for this purpose is described in EP-A-224947 in the name of The Dow Chemical Company.

In the method according to the invention the preshaped porous material, which is given the desired physical and thermal properties by means of known techniques, is loaded with (a precursor of) the catalytically active component and optionally the promoter. In general this is carried out by means of impregnation with a solution of the component to be loaded or a precursor thereof. The starting compound to be used for the impregnation may be any compound of the metal present in the component to be loaded which is able to dissolve or form a complex in the impregnation solvent. According to the invention it is preferred to impregnate with a solution containing a complex of the component to be loaded and in particular of the catalytically active component or a precursor thereof, the viscosity of which solution preferably does not decrease and most preferably increases while heating and/or vaporizing the solvent. Thereafter, the solvent is vaporized and the complex of the catalytically active component or precursor thereof is decomposed, for example by means of heating. Suitable complexing agents are, for example, ethylene diamine tetraacetate (EDTA), citric acid, lactic acid, oxalic acid, formic acid, gluconic acid and other complexing agents yielding a complex which badly crystallizes.

Preferably the catalytically active component or precursor thereof is complexed with citric acid or with EDTA. In case iron oxide is applied as active component, preferably ammonium-iron(III)-EDTA or ammonium-iron(III)-citrate is used as impregnating complex. Depending on the specific type of preshaped porous support material and on the solubility of the complex in the impregnating solution, only a limited amount of the component to be loaded can be applied per impregnation step. This amount to be maximally applied per impregnation step varies in general between 0.1 and 5 weight percent, calculated as the zero-valent metal component and based on the total catalyst weight. Therefore, it may be necessary or desirable to repeat a certain impregnation step, such as for example in case a high loading is desired. The impregnation step for applying the catalytically active component may also be combined with the impregnation step for applying a promoter.

In the method according to the invention it is preferred to use an impregnation solution of potassium carbonate for applying the optional promoter to the preshaped support body.

According to a further preferred embodiment of the method according to the invention in each impregnation step a quantity of solution is used which essentially corresponds to the pore volume of the support material to be impregnated.

Particularly good results are obtained when the preshaped support material is evacuated prior to the impregnation step. The evacuation or in other words the step of applying a vacuum is advantageously carried out at elevated temperature. By evacuating the support material in the impregnation step, the pores can be filled quickly.

The removal of the solvent used in the impregnation step may be achieved in any suitable manner. It has been found appropriate to first dry the impregnated support bodies at room temperature and subsequently at elevated temperature, for example from 50° to 150° C.

After the solvent used in the impregnation step has been removed, the impregnated support body is preferably subjected to a temperature in the range of 500° to 1000° C. and more preferably 500°–800° C. in order to remove the complexing agents and other agents used in the impregnation step (in as far as this has not yet taken place in the drying step). Most preferably, the impregnated support material is heated to a temperature of 650°–750° C. Usually this is done in an oxidizing atmosphere, optionally followed by treatment in a reducing atmosphere. As oxidizing atmosphere for example oxygen or air may be used and as reducing atmosphere for example hydrogen gas, ammonia or carbon monoxide may be used. If desired, also other reducing agents or oxidizing agents may be used. The freshly prepared catalyst may be subjected to conventional treatments in order to convert the catalyst components to the active species or to species which are converted to such active species under reaction conditions.

Surprisingly, it has been discovered that by exposing the freshly prepared catalyst containing a promoter to a water vapor containing atmosphere, the promoter becomes highly dispersed, resulting in a strongly suppressed carbon deposition on the catalyst.

According to a final aspect the present invention relates to the use of the catalyst described herein in the dehydrogenation of hydrocarbons.

As described hereinbefore, the dehydrogenation of hydrocarbons is a process used frequently and on a large scale. Often, the product of the dehydrogenation process is a bulk chemical produced in an amount of more than 100,000 tons per year per reactor. Such processes thus require voluminous catalyst beds through which the hydrocarbon to be dehydrogenated is passed, mostly at a high temperature. Now it has been found, that the catalyst according to the present invention possesses the mechanical and thermal stability required for such large scale dehydrogenation processes. This enables the present catalyst to be used for long periods of time in large catalyst beds without having to replace the catalyst bed due to mechanical deterioration of the catalyst bed, which from an economical point of view is advantageous.

The catalyst according to the invention can be used in a variety of catalytic dehydrogenation processes for hydrocarbons and organic compounds, which are optionally substituted, under conditions which may be oxidative or not. Examples of compounds which may so be dehydrogenated are alkanes, alkenes, cycloalkanes, alkyl-aromatic compounds, alkyl-heterocyclic compounds, alkenyl cycloalkanes or -alkenes, alkylhalides, ketones, aldehydes, alcohols, ethers, carboxylic acids, esters, amines and nitriles.

The use of the catalyst in the dehydrogenation of ethylbenzene to styrene and of butene to 1, 3-butadiene is preferred.

Preferably, the catalyst according to the present invention to which an alkali metal and/or an alkaline earth metal compound has been applied as promoter is used in a dehydrogenation process which is carried out in the presence of steam and at temperatures in the range of 400° to 800° C.

The catalyst according to the invention to which no promoter has been applied is preferably used under conditions where substantially no carbon deposits on the catalyst occur or where these carbon deposits are removed in another way, such as for example in oxidative dehydrogenation reactions.

Hereinafter, the invention will be illustrated by means of the examples which by no means should be construed to limit the invention.

EXAMPLE 1

A catalyst consisting of preshaped magnesium oxide tablets having applied thereto 3.1 wt.% of iron and 3 wt.% of potassium, based on the total catalyst weight, was prepared by impregnation with a solution of ammonium iron citrate and then of potassium carbonate.

The magnesium oxide tablets having dimensions of about 3.6 mm in height and 3.2 mm in diameter, had a specific surface area of 8 $m^2$ per gram and a cumulative pore volume of 0.346 $cm^3$ per gram. The impregnation solution for applying of iron (solution A) was prepared by dissolving 59.6 grams of ammonium iron citrate in water and by adding water up to 100 ml. The impregnation solution for applying potassium (solution B) was prepared by dissolving 15.8 grams of anhydrous potassium carbonate in water and by adding water up to 100 ml.

Before the impregnation, the preshaped support material was evacuated. Subsequently, solution A was used for the first impregnation. Per 100 gram of magnesium oxide 34.6 ml of solution was impregnated. The impregnation was followed by drying at room temperature during 24 hours, then by drying in air at 120° C. Thereafter, the precursor was decomposed to the respective oxide by heating it in air at 700° C. Finally, after evacuation solution B was used for impregnation. The latter impregnation was followed by the same post-treatment as in case of solution A.

EXAMPLE 2

In the same manner as described in Example 1 a catalyst was prepared, except that now only 1.1 wt.% of iron and 3 wt.% of potassium were applied to the preshaped magnesium oxide carrier bodies.

An impregnation solution (solution C), prepared by dissolving 19.5 grams of ammonium iron citrate in water and by adding water up to 100 ml, was used for applying iron, whereas for applying of 3 wt.% of potassium solution B of Example 1 was used for the impregnation.

EXAMPLE 3

In the same manner as described in Example 1 a catalyst was prepared, except that now 4.4 wt.% of iron and 3 wt.% of potassium were applied as ammonium iron-EDTA and potassium carbonate, respectively. By means of a first impregnation with solution D, 2.8 wt.% of iron was applied. By means of a second impregnation with solution E, the further amount of iron (1.6 wt.%) and 3 wt.% of potassium were applied simultaneously.

Solution D was prepared by suspending 63.7 grams of ammonium iron-EDTA in water. Subsequently, this suspension was dissolved with the help of concentrated ammonia until a pH-value of about 6.5 was obtained, after which water was added until 100 ml. The second impregnation solution E was prepared by dissolving 15.8 grams of anhydrous potassium carbonate in water. 63.7 grams of ammonium iron-EDTA were suspended in this solution, and subsequently dissolved by adding concentrated ammonia until a pH-value of about 6.5. Finally water was added until 100 ml. After the first and second impregnation a post-treatment was carried out each time as described in Example 1.

EXAMPLE 4

In this Example the mechanical strength was measured for the catalysts according to Examples 1 and 3 (according to the invention) and also for the commercial Shell S-105 dehydrogenation catalyst (comparative experiment). The fresh Shell S-105 catalyst had the following composition: 88.0 wt.% of $Fe_2O_3$, 9.5 wt.% of $K_2O$ and 2.5 wt.% of $Cr_2O_3$. The mechanical strength was measured as the side crush strength according to ASTM method D-4179-82 on a Schleuninger Tablet Hardness Tester, Model 4M. The values for the side crush strength have been normalized in order to correct for the different particle sizes.

In fresh condition, the catalyst according to Example 1 had a side crush strength of 10.8±3.1 $N/mm^2$. After using this catalyst for about 250 hours in the dehydrogenation of ethylbenzene, the side crush strength was measured again; this now was 13.8±4.1 $N/mm^2$. Therefore, during use the mechanical strength was found to increase somewhat.

The side crush strength of the catalyst of Example 3 was also measured in fresh condition, which was found to have a value of 10.1±4.5 $N/mm^2$.

The side crush strength of the fresh Shell S-105 catalyst, having an extrudate diameter of 3.2 mm (⅛ inch) lies between 8.5 and 10.5 $N/mm^2$. The side crush strength was also measured for a Shell S-105 catalyst which has already been used in a commercial ethylbenzene dehydrogenation reactor for a year. Before the measurements, the used catalyst was separated from the fines formed in the reactor by means of sieving. The value of the side crush strength after use was 7±3 $N/mm^2$. It should be noted here that this latter value gives a somewhat misleading picture as the catalyst used for this experiment consisted (even after sieving) of particles having a relatively hard core and a relatively soft enclosure, caused by the migration of the potassium. During the strength measurement the enclosure was found to disintegrate quickly without giving a strength value output. Therefore, the above-mentioned value is the value at which the relatively hard core disintegrates or breaks.

EXAMPLE 5

The performance of the catalysts according to the invention prepared in Examples 1 and 3 was tested in the dehydrogenation of 1-butene to 1, 3-butadiene. For comparative purposes also the commercial Shell S-105 catalyst was tested. The experiments were carried out in a lab scale reactor at atmospheric pressure, whereby a gas phase having the composition; 5 vol.% 1-butene, 30 vol.% water vapor and 65 vol.% nitrogen was passed with a flow velocity of 50 ml/min over 1 gram of the above-mentioned catalysts. The Examples were carried out at temperatures varying from 425° to 650° C.

The terms selectivity, conversion and yield as used herein are defined as follows:

selectivity=(number of moles of 1, 3-butadiene formed)/(number of moles of 1-butene converted)×100% conversion=(number of moles of 1-butene converted)/(number of moles of 1-butene used)×100% yield=selectivity×conversion / 100%

The results of these experiments are shown in FIG. 1-7.

It appears from these results that the catalyst according to the present invention, throughout the complete tested temperature range, gives results similar to those of the commercial Shell S-105 catalyst in the dehydrogenation of 1-butene.

EXAMPLE 6

In this Example the catalyst according to Example 1 (invention) and the Shell S-105 catalyst (comparison) were tested in a lab rig for the dehydrogenation of ethylbenzene to styrene.

The experiments were carried out in a tubular reactor having an inner diameter of 2.5 cm, in which circa 70 ml catalyst was introduced. Steam and ethylbenzene were fed in a weight ratio steam/ethylbenzene of 1.1 and at a LHSV of 0.9. The pressure in the reactor was 1.2 bar, whereas the temperature was varied between 560° and 640° C.

Figure 1:
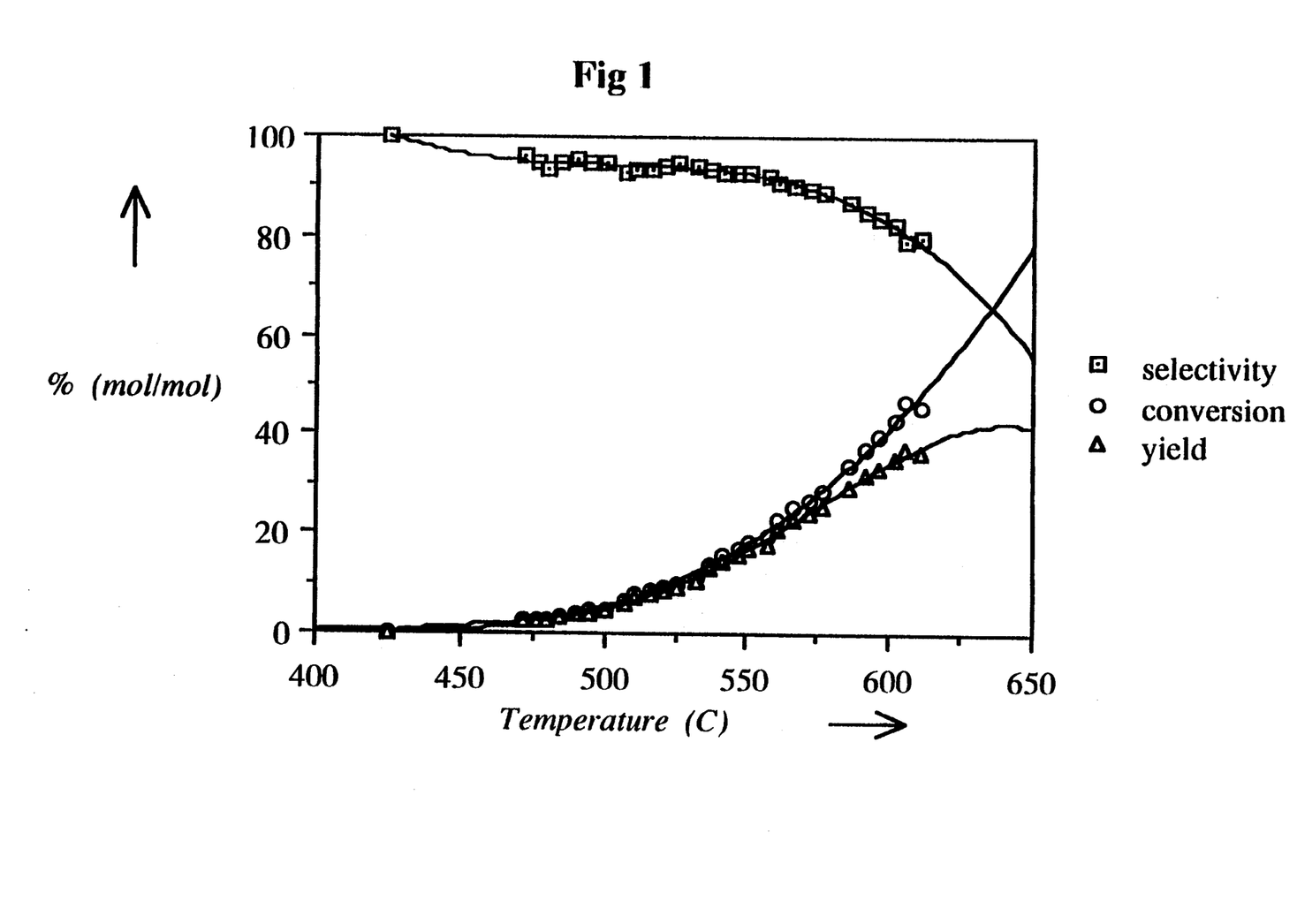
FIG. 1 shows the selectivity, conversion and yield as a function of the temperature for the catalyst according to Example 1.
Figure 2:
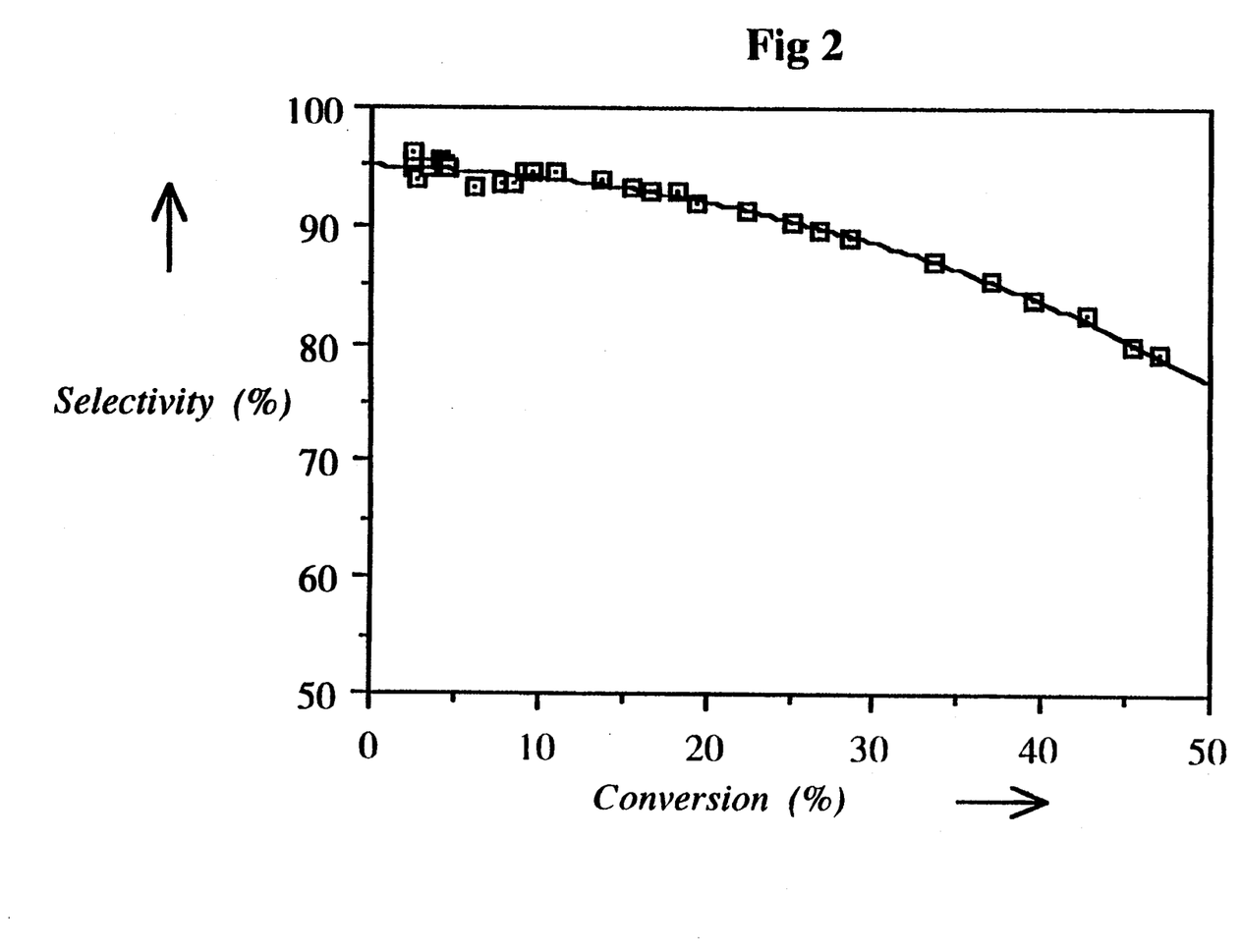
FIG. 2 shows the relationship between the selectivity and the conversion for the catalyst according to Example 1.
Figure 3:
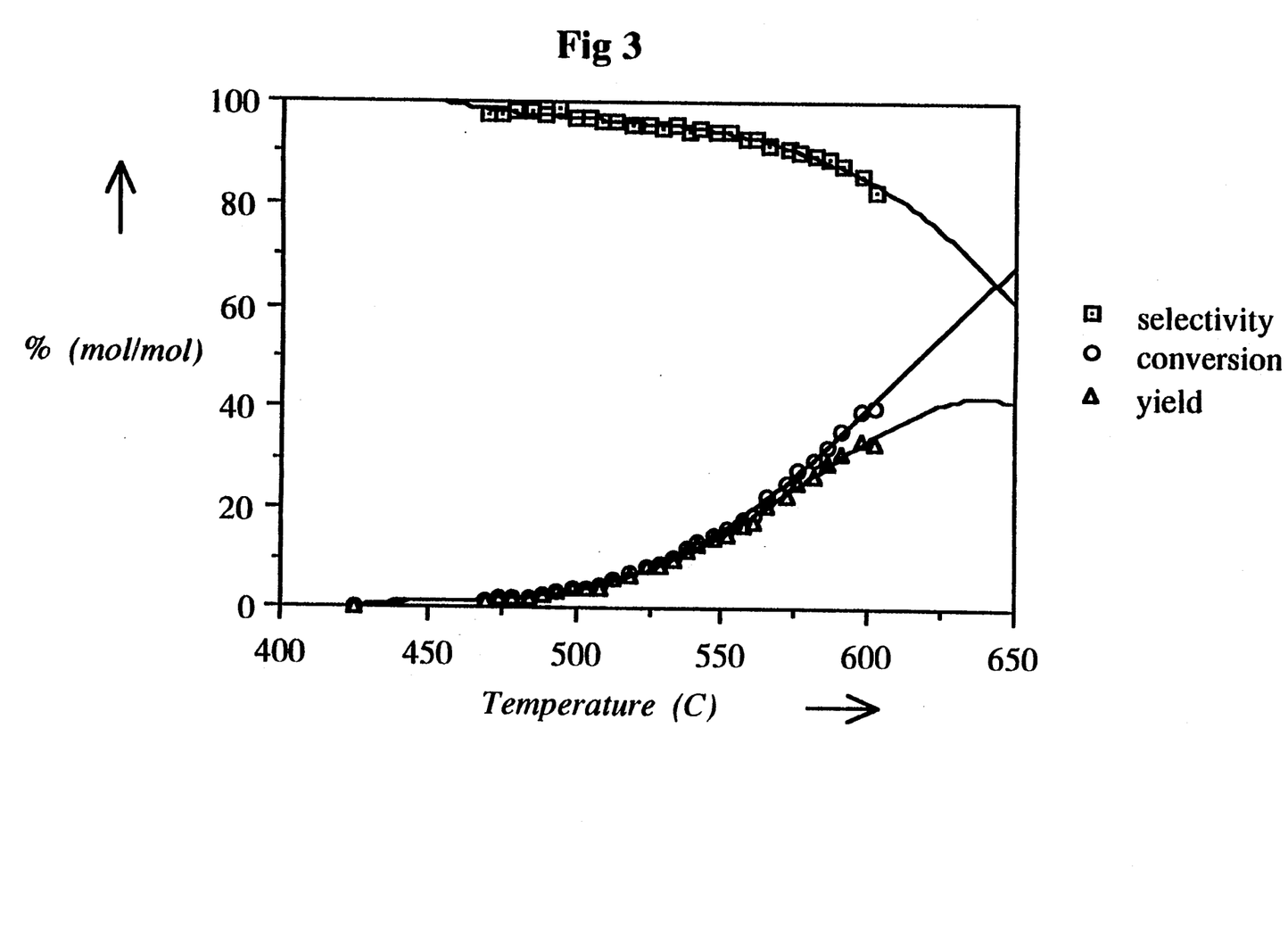
FIG. 3 shows the selectivity, conversion and yield as a function of the temperature for the catalyst according to Example 3.
Figure 4:
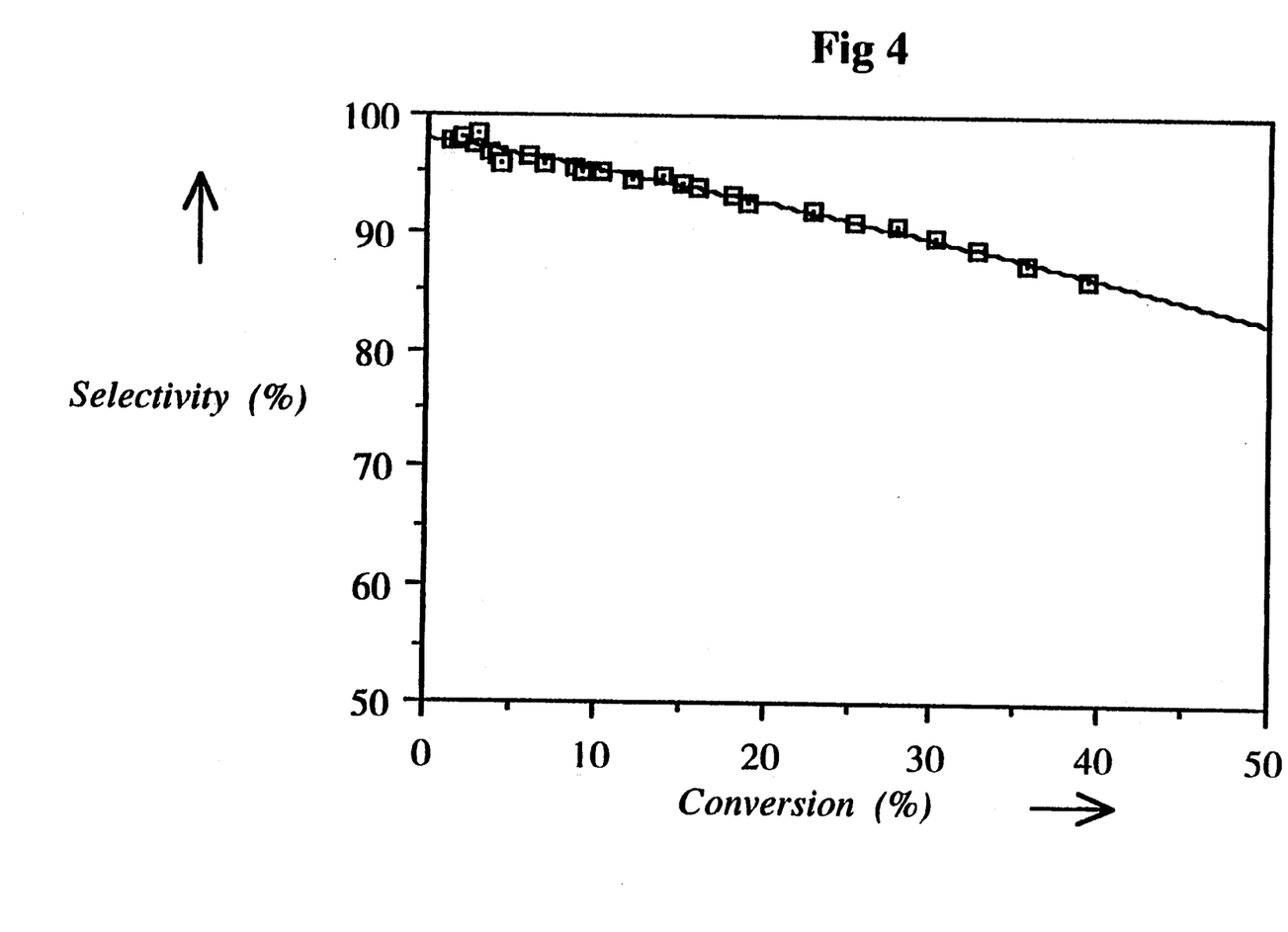
FIG. 4 shows the relationship between the selectivity and conversion for the catalyst according to Example 3.
Figure 5:
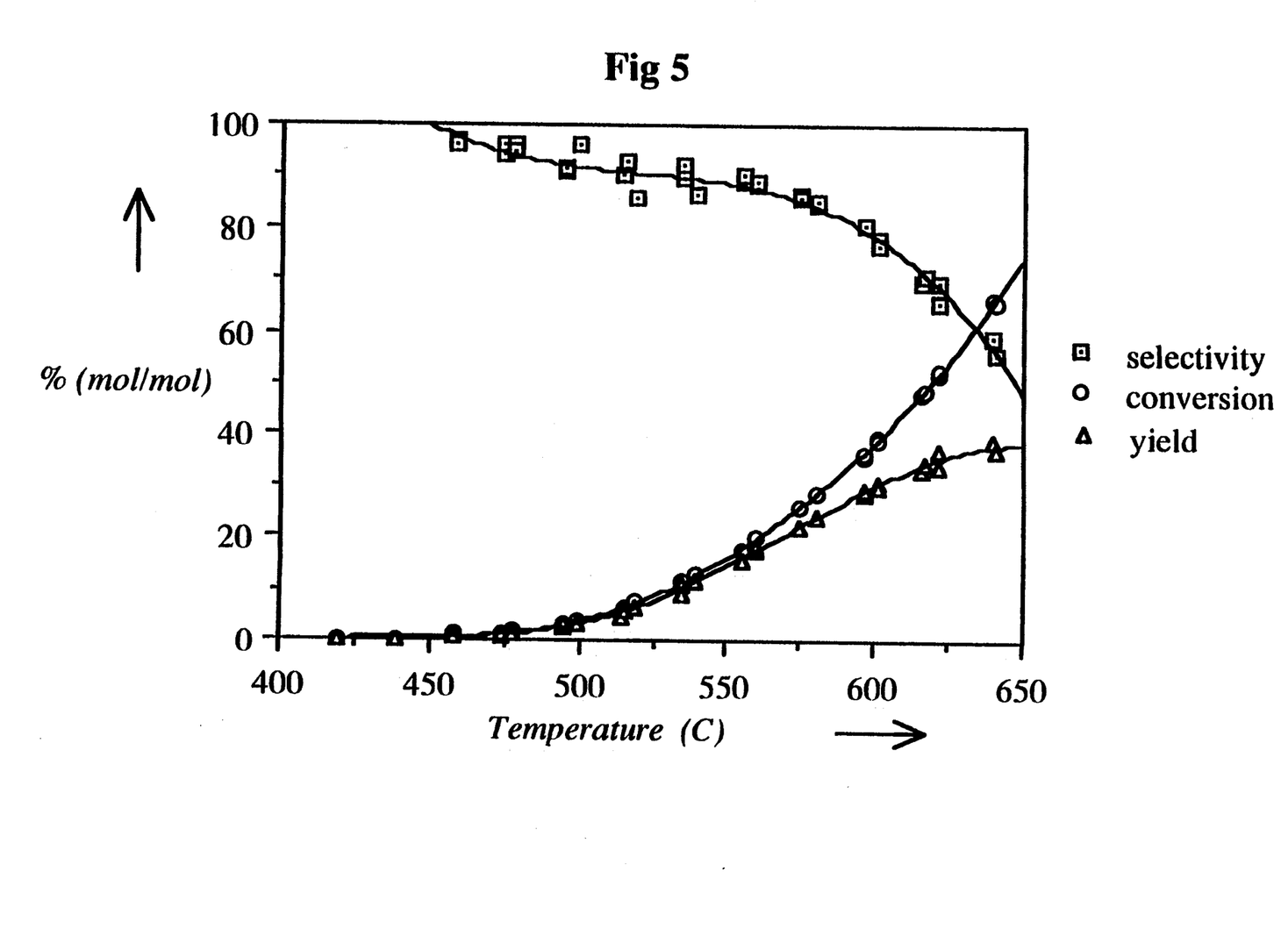
FIG. 5 shows the selectivity, conversion and yield for the Shell S-105 catalyst as a function of the temperature.
Figure 6:
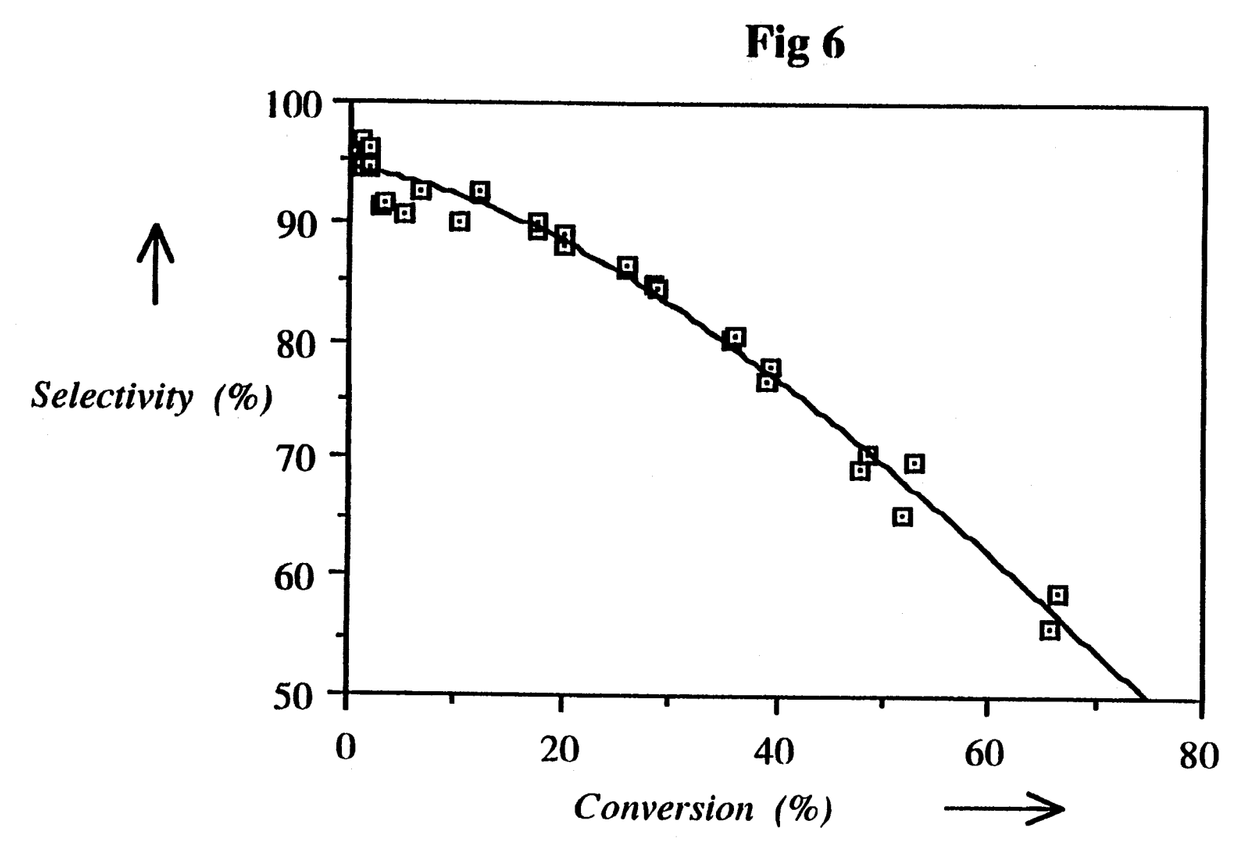
FIG. 6 shows the relationship between the selectivity and conversion for the Shell S-105 catalyst.
Figure 7:
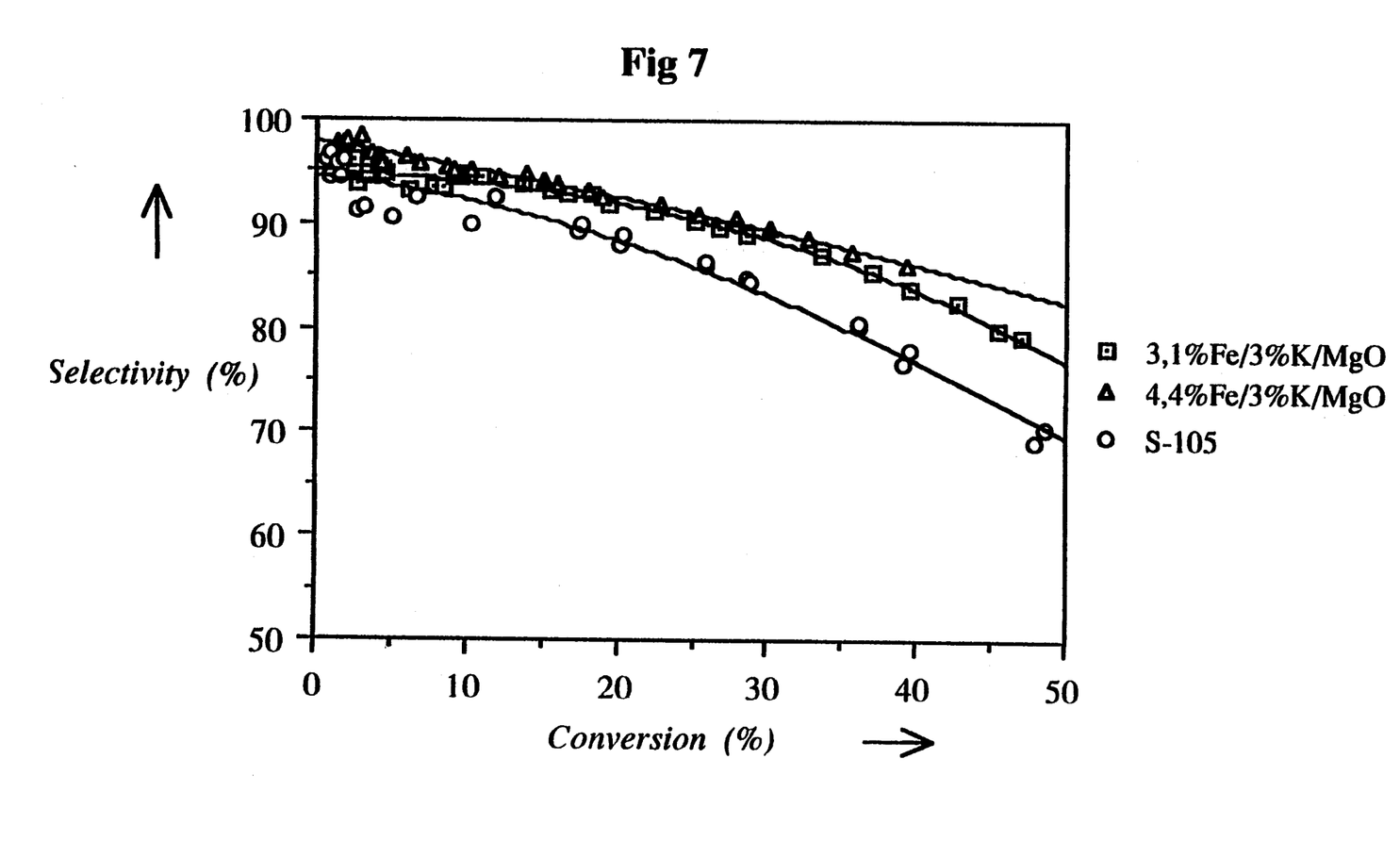
FIG. 7 shows the graphs of FIGS. 2, 4 and 6 together.
Figure 8:
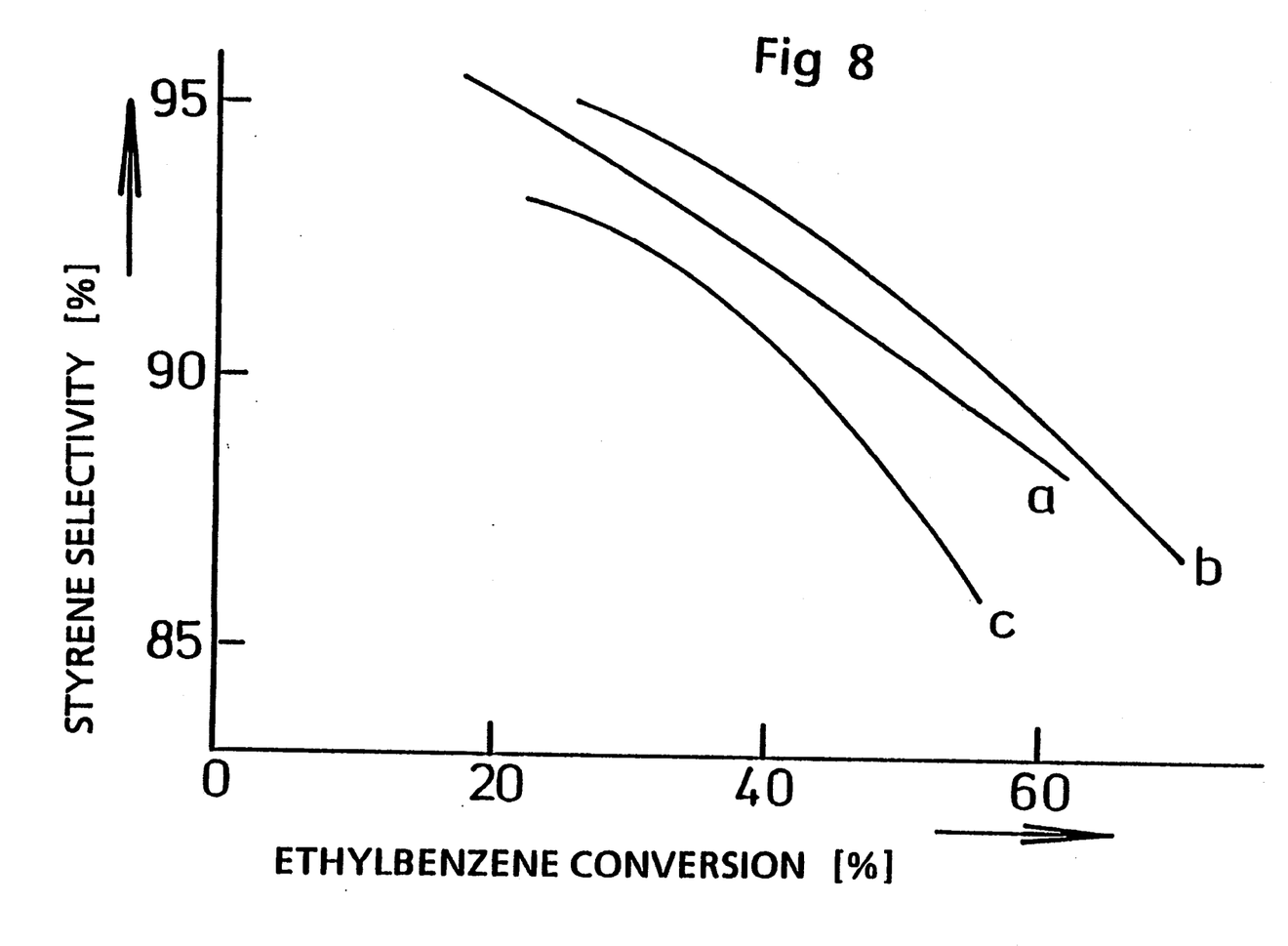
FIG. 8 shows the relationship between selectivity and conversion for the dehydrogenation of ethylbenzene to styrene using the catalyst according to Example 1 and fresh or used Shell S-105 catalyst.

In FIG. 8 the relationship between selectivity and conversion is shown. In FIG. 8 graph a depicts the results for the catalyst according to the invention; graph b gives the results for the fresh Shell S-105 catalyst, and graph c for the used Shell S-105 catalyst (as described in Example 4).

During a test of more than 130 hours, wherein the steam/ethylbenzene ratio in the feed at first was maintained during circa 60 hours at 1.5 at a constant conversion of 41%, and later during about 60 hours at a ratio of 0.84 at a constant conversion of 26%, no deactivation of the catalyst according to Example 1 was detected. The styrene selectivities at the steam/ethylbenzene ratios mentioned were 93 mole % (for ratio of 1.5) and 95 mole % (for ratio of 0.84), respectively.

EXAMPLE 7

In this Example the bulk crushing strength (BCS) was measured for a catalyst comprising the magnesium oxide support as defined in Example 1 to which 6 wt.% iron and 6 wt.% potassium have been applied by the simultaneous impregnation with a solution of ammonium iron citrate and potassium carbonate analogous to Example 3. The BCS was measured for both the fresh catalyst and the same catalyst which has been used in an ethylbenzene dehydrogenation test for 4 weeks, in which test the reactor temperature was varied between 540° and 640° C.

The BCS is defined as the pressure (in MPa) exerted by a plunger on a catalyst sample contained in a cylinder, at which pressure the quantity of fines, formed as a result of that pressure and passing through a 425 μm sieve, amounts to 0.5 % (m/m) of the sample.

The apparatus used in the test was obtained from the company Gémécanique, Rueil, France. The test procedure was as follows.

After drying for two hours at 300° C. and cooling down in a dessicator containing silicagel, the sample was sieved to remove the fines (425μm sieve). The remaining quantity of catalyst (21.3635 g for fresh catalyst; 28.4233 g for used catalyst) was transferred to the sample holder (inside diameter 27.6 mm, height 50 mm, cross-sectional area 600 mm$^2$) and covered with steel balls (approximately 5 ml). The plunger then was moved down slowly until a force of 10 daN (1 daN=10 N) corresponding to a pressure of 0.1667 MPa was reached, which pressure was maintained for three minutes. Subsequently, the plunger was moved upwards and the steel balls removed. The content of the sample holder was transferred onto the 425 μm sieve, and after sieving for about 6 minutes the fines were collected and weighed. This procedure was repeated five more times whereby the applied force was each time increased to 20, 40, 60, 80 and 100 daN, respectively, which forces correspond to pressures of 0.333, 0.6667, 1.000, 1.333 and 1.667 MPa, respectively. The pressure relates to the force according to the formula $$\text{pressure [MPa]} = \frac{\text{force [daN]} \times 10}{600 \text{ mm}^2}$$

Each time the amount of fines weighed. The results are summarized in the following Table.

| Force Applied [daN] | Pressure [MPa] | % fines* fresh catalyst | % fines* used catalyst |
|---|---|---|---|
| 10 | 0.1667 | 0.0126 | 0.0352 |
| 20 | 0.3333 | 0.0496 | 0.0482 |
| 40 | 0.6667 | 0.0917 | 0.0894 |
| 60 | 1.000 | 0.4054 | 0.1488 |
| 80 | 1.333 | 0.6914 | 0.2779 |
| 100 | 1.667 | 1.0218 | 0.4306 |

*% fines is calculated according to (m$_i$/m$_s$) ×0 100, where
m$_i$ = cumulative mass of fines, [g]
m$_s$ = mass of sample, [g]

Figure 9:
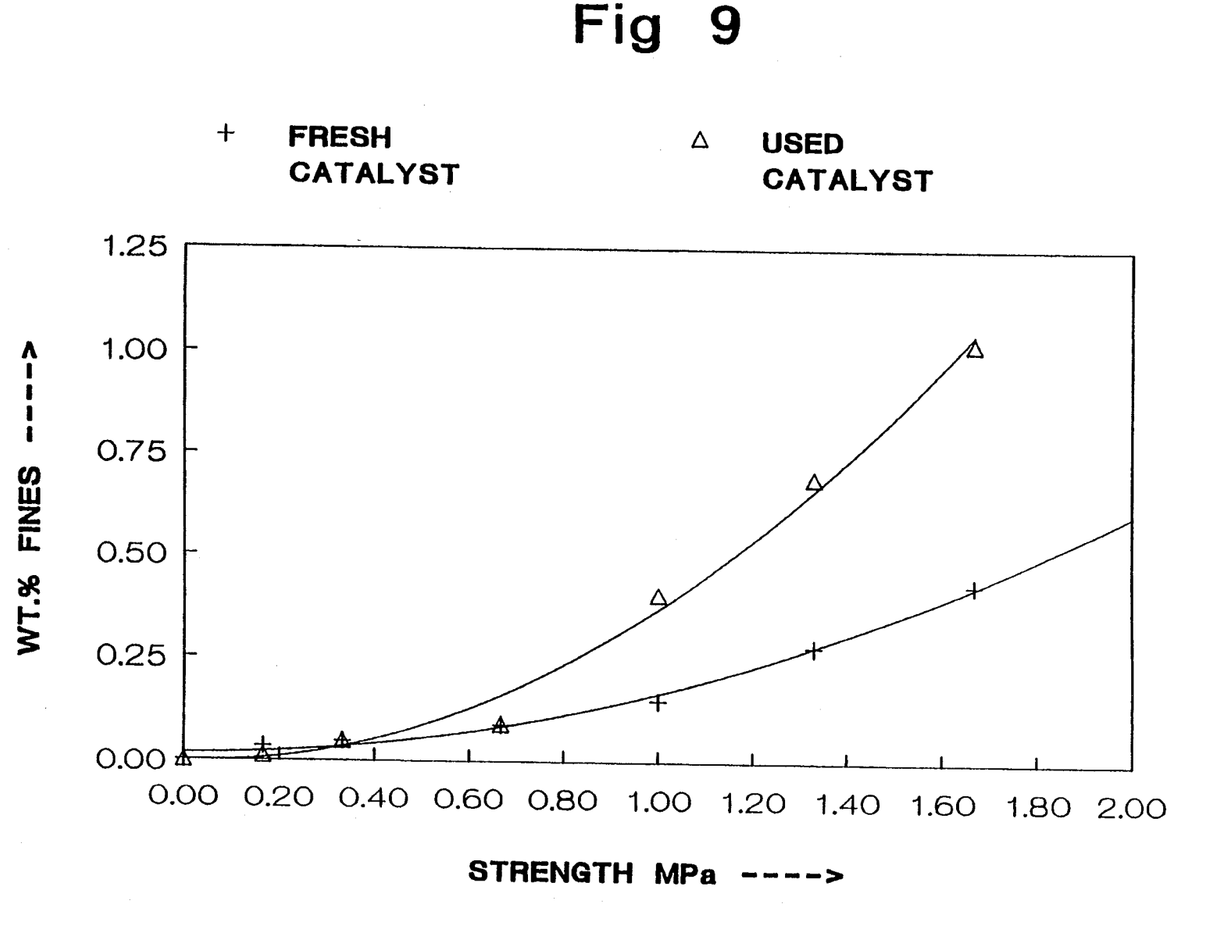
FIG. 9 shows the relationship between the bulk crushing strength and the weight % fines of the fresh and used catalyst of the invention.

As can be seen from FIG. 9, in which these results are illustrates graphically, the bulk crushing strength of the used catalyst has increased compared to the value for the fresh catalyst.

We claim:

1. A process for the dehydrogenation of hydrocarbons, under dehydrogenation conditions, in the presence of steam at a temperature in the range of 400°–800° C. which process comprises using a catalyst comprising a preshaped porous support material, said preshaped porous support material being obtained by subjecting a corresponding powderous support material to a shaping operation and/or thermal treatment causing sintering of powder particles, and having a specific surface area of from 0.1 to 50 m²/g, at least a catalytically active component chosen from the group consisting of compounds of the transition metals vanadium chromium manganese, iron, cobalt nickel, copper and zinc in an amount of from 0.1 to 20 wt.%, the amount being calculated as metal based on the total catalyst weight, said compounds being applied to the support in a finely divided form by impregnation.

2. The process according to claim 1 wherein the preshaped porous support material has an average diameter of at least 0.5 mm.

3. The process according to claim 2 wherein the preshaped porous support material has a specific surface area of from 0.1 to 25 m²/gram and an average diameter of from 1 to 20 mm.

4. The process according to claim 1 wherein the preshaped porous support material is magnesium oxide.

5. The process according to claim 1 wherein the catalytically active component contains at least an oxide of iron.

6. The process according to claim 1 wherein the catalyst further comprises at least an alkali metal and/or alkaline earth metal compound as promoter in an amount of from 0.1 to 20 wt. %, the amount being calculated as metal based on the total catalyst weight, said promoter being applied to the support in a finely divided form by impregnation.

7. The process according to claim 6, wherein a hydroxide, oxide or carbonate of potassium has been applied as promoter.

8. The process according to claim 1 comprising dehydrogenating ethylbenzene to styrene or butene to 1,3-butadiene.

9. A process for the dehydrogenation of hydrocarbons, under dehydrogenation conditions, in the presence of steam at a temperature in the range of 400°-800° C. which process comprises using a catalyst comprising a preshaped porous support material, said preshaped porous support material being obtained by subjecting a corresponding powderous support material to a shaping operation and/or thermal treatment causing sintering of powder particles, and having a specific surface area of from 0.1 to 50 m²/g, at least a catalytically active component chosen from the group consisting of compounds of the transition metals vanadium, chromium, manganese, iron, cobalt, nickel, copper and zinc in an amount of from 0.1 to 20 wt.%, the amount being calculated as metal based on the total catalyst weight, said compounds being applied to the support in a finely divided form by impregnation, with the proviso that the catalytically active component contains at least an oxide of iron.

10. The process according to claim 9, wherein the preshaped porous support material has an average diameter of at least 0.5 mm.

11. The process according to claim 10 wherein the preshaped porous support material has a specific surface area of from 0.1 to 25 m²/gram and an average diameter of from 1 to 20 mm.

12. The process according to claim 9 wherein the preshaped porous support material is magnesium oxide.

13. The process according to claim 9 wherein the catalyst further comprises at least an alkali metal and/or alkaline earth metal compound as promoter in an amount of from 0.1 to 20 wt.%, the amount being calculated as metal based on the total catalyst weight, said promoter being applied to the support in a finely divided form by impregnation.

14. The process according to claim 9 wherein a hydroxide, oxide or carbonate of potassium has been applied as promoter.

15. The process according to claim 9 comprising dehydrogenating ethylbenzene to styrene.

16. The process according to claim 9 comprising dehydrogenating butene to 1,3- butadiene.

17. A process for the dehydrogenation of hydrocarbons, under dehydrogenation conditions, in the presence of steam at a temperature in the range of 400°-800° C. which process comprises using a catalyst comprising a preshaped porous support material, said preshaped porous support material being obtained by subjecting a corresponding powderous support material to a shaping operation and/or thermal treatment causing sintering of powder particles, and having a specific surface area of from 0.1 to 50 m²/g, at least a catalytically active component consisting essentially of one or more compounds chosen from the group consisting of compounds of the transition metals vanadium, chromium manganese, iron, cobalt, nickel, copper and zinc in an amount of from 0.1 to 20 wt.%, the amount being calculated as metal based on the total catalyst weight, said compounds being applied to the support in a finely divided form by impregnation.

18. The process according to claim 17 wherein the the preshaped porous support material has an average diameter of at least 0.5 mm and a specific surface area of from 0.1 to 25 m²/gram.

19. The process of claim 17 wherein the preshaped porous support material is magnesium oxide and the catalytically active component contains at least an oxide of iron.

20. The process according to claim 17 wherein the catalyst further comprises at least an alkali metal and/or alkaline earth metal compound as promoter in an amount of from 0.1 to 20 wt.%, the amount being calculated as metal based on the total catalyst weight, said promoter being applied to the support in a finely divided form by impregnation.

* * * * *